US009867908B2

(12) United States Patent
Lareau et al.

(10) Patent No.: US 9,867,908 B2
(45) Date of Patent: *Jan. 16, 2018

(54) DIALYSIS CATHETERS WITH FLUOROPOLYMER ADDITIVES

(71) Applicant: ANGIODYNAMICS, INC., Latham, NY (US)

(72) Inventors: Raymond Lareau, Westford, MA (US); Benjamin Bell, Shrewsbury, MA (US); Jeannette Ho, Toronto (CA); J. Paul Santerre, Whitby (CA); Carol Lancette, Fort Ann, NY (US); Theodore Beyer, Queensbury, NY (US); William Appling, Granville, NY (US)

(73) Assignee: ANGIODYNAMICS, INC., Latham, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/132,116

(22) Filed: Apr. 18, 2016

(65) Prior Publication Data

US 2016/0228616 A1 Aug. 11, 2016

Related U.S. Application Data

(60) Continuation of application No. 14/220,572, filed on Mar. 20, 2014, now abandoned, which is a continuation-in-part of application No. 14/100,671, filed on Dec. 9, 2013, now Pat. No. 8,876,797, which is a continuation of application No. 13/950,592, filed on Jul. 25, 2013, now Pat. No. 8,603,070, said application No. 14/220,572 is a continuation-in-part of application No. 14/151,267, filed on Jan. 9, 2014, which is a continuation of application No. 12/392,220, filed on Feb. 25, 2009, now abandoned, which is a division of application No. 11/557,369, filed on Nov. 7, 2006, now Pat. No. 8,317,773.

(60) Provisional application No. 61/790,821, filed on Mar. 15, 2013.

(51) Int. Cl.
| | |
|---|---|
| A61L 29/18 | (2006.01) |
| A61M 1/36 | (2006.01) |
| A61L 29/06 | (2006.01) |
| A61M 25/00 | (2006.01) |
| A61L 29/04 | (2006.01) |
| A61L 29/14 | (2006.01) |

(52) U.S. Cl.
CPC ............ *A61L 29/06* (2013.01); *A61L 29/041* (2013.01); *A61L 29/14* (2013.01); *A61L 29/18* (2013.01); *A61M 1/3653* (2013.01); *A61M 25/0071* (2013.01); *A61M 2025/0031* (2013.01); *A61M 2025/0073* (2013.01)

(58) Field of Classification Search
None
See application file for complete search history.

(56) References Cited

U.S. PATENT DOCUMENTS

| | | |
|---|---|---|
| 3,392,183 A | 7/1968 | Erwin et al. |
| 3,427,366 A | 2/1969 | Verdol et al. |
| 3,872,058 A | 3/1975 | Gresham |
| 4,312,907 A | 1/1982 | Hiraoka et al. |
| 4,584,362 A | 4/1986 | Leckart et al. |
| 4,661,530 A | 4/1987 | Gogolewski et al. |
| 4,742,090 A | 5/1988 | Hunter et al. |
| 4,788,083 A | 11/1988 | Dammann et al. |
| 4,792,354 A | 12/1988 | Matsuo et al. |
| 4,861,830 A | 8/1989 | Ward, Jr. |
| 4,994,503 A | 2/1991 | Harris et al. |
| 5,064,871 A | 11/1991 | Sciangola |
| 5,145,727 A | 9/1992 | Potts et al. |
| 5,149,576 A | 9/1992 | Potts et al. |
| 5,242,995 A | 9/1993 | Kim et al. |
| 5,395,525 A | 3/1995 | Takano et al. |
| 5,486,570 A | 1/1996 | St. Clair |
| 5,542,200 A | 8/1996 | Matsuoka |
| 5,543,200 A | 8/1996 | Hargis et al. |
| 5,589,563 A | 12/1996 | Ward et al. |
| 5,779,897 A | 7/1998 | Kalthod et al. |
| 5,795,326 A | 8/1998 | Siman |

(Continued)

OTHER PUBLICATIONS

Jahangir et al., "Fluorinated surface-modifying macromolecules: modulating adhesive protein and platelet interactions on a polyether-urethane", Journal of Biomedical Materials Research Part A, 60, 135-137, Apr. 2002.*
Salis et al., Can Peripherally Inserted Central Catheters be Used for Contrast Injection with a CT Power Injector?, JVIR vol. 13, Issue 2, Feb. 2002, Supplement S1.
Garland et al., Measurement of Extravascular Lung Water in Hemodialysis Patients Using Blood Ultrasound Velocity and Optical Density Dilution, American Society of Artificial Internal Organs Journal, 2002, pp. 398-403.

(Continued)

*Primary Examiner* — Christopher M Rodd

(57) ABSTRACT

A vascular access catheter is disclosed that has a catheter shaft with a distal end portion with a distal tip having a sloped face that is positioned at an acute angle from the distal tip relative to a longitudinal axis of the catheter shaft. A first, second, and third lumen extend longitudinally through the catheter shaft. The third lumen is configured for receiving a guidewire and may extend a partial length of the catheter or substantially the entire length of the catheter. The first lumen has an aperture located in the angled edge distal end portion of the catheter next to the distal tip and communicates with the first lumen. The second lumen has an aperture that is positioned in the outer surface of the catheter shaft that is in communication with the second lumen, and is spaced proximally from the first lumen aperture. The catheter includes a fluoropolymer additive with specific compositions and/or purity levels.

21 Claims, 8 Drawing Sheets

(56) References Cited

U.S. PATENT DOCUMENTS

| | | | |
|---|---|---|---|
| 5,879,499 A * | 3/1999 | Corvi | A61M 25/0012 |
| | | | 156/173 |
| 5,908,701 A | 6/1999 | Jennings et al. | |
| 5,929,201 A | 7/1999 | Gibbons et al. | |
| 5,954,966 A | 9/1999 | Matsuura et al. | |
| 6,111,049 A | 8/2000 | Sendijarevic et al. | |
| 6,127,485 A | 10/2000 | Klun et al. | |
| 6,127,507 A * | 10/2000 | Santerre | A61L 33/0076 |
| | | | 428/423.1 |
| 6,254,645 B1 | 7/2001 | Kellis, Jr. et al. | |
| 6,353,057 B1 | 3/2002 | He et al. | |
| 6,448,364 B1 | 9/2002 | Clatty et al. | |
| 8,071,683 B2 | 12/2011 | Mullick et al. | |
| 8,178,620 B2 | 5/2012 | Mullick et al. | |
| 8,187,234 B2 | 5/2012 | Weaver et al. | |
| 8,267,915 B2 | 9/2012 | Daly et al. | |
| 8,317,773 B2 | 11/2012 | Appling et al. | |
| 8,318,867 B2 | 11/2012 | Mullick et al. | |
| 8,338,537 B2 | 12/2012 | Mullick et al. | |
| 8,377,011 B2 | 2/2013 | Weaver et al. | |
| 8,603,070 B1 * | 12/2013 | Lareau | A61L 29/049 |
| | | | 524/423 |
| 8,784,402 B1 | 7/2014 | Lareau et al. | |
| 8,876,797 B2 | 11/2014 | Lareau et al. | |
| 8,877,062 B2 | 11/2014 | Mullick et al. | |
| 9,206,283 B1 | 12/2015 | Santerre et al. | |
| 2004/0121175 A1 | 6/2004 | Flexman et al. | |
| 2005/0171490 A1 | 8/2005 | Weaver et al. | |
| 2005/0171510 A1 | 8/2005 | DiCarlo et al. | |
| 2005/0176893 A1 | 8/2005 | Rana et al. | |
| 2007/0037891 A1 | 2/2007 | Esfand et al. | |
| 2008/0154186 A1 * | 6/2008 | Appling | A61M 25/003 |
| | | | 604/43 |
| 2008/0228253 A1 * | 9/2008 | Mullick | C08G 18/10 |
| | | | 623/1.1 |
| 2009/0211968 A1 | 8/2009 | Ho et al. | |
| 2011/0009799 A1 | 1/2011 | Mullick et al. | |
| 2011/0207893 A1 | 8/2011 | Mullick et al. | |
| 2012/0148774 A1 | 6/2012 | Mullick et al. | |
| 2012/0220724 A1 | 8/2012 | Mullick et al. | |
| 2013/0158488 A1 | 6/2013 | Weaver et al. | |
| 2014/0128848 A1 | 5/2014 | Appling et al. | |
| 2014/0276470 A1 | 9/2014 | Lareau et al. | |
| 2015/0025198 A1 | 1/2015 | Mullick et al. | |
| 2015/0038946 A1 | 2/2015 | Lareau et al. | |

OTHER PUBLICATIONS

Teichgraber et al., Central Venous Access Catheters: Radiological Management of Complications, Cardiovascular and Interventional Radiology, Jul. 31, 2003, pp. 321-333.

Glickman et al., Challenges of hemodialysis access for high risk patients: Impact of mesenteric vein bioprosthetic graft, The Journal of Vascular Access, 2003 pp. 73-80.

Choi et al., Peritoneal Dialysis, Medicine, 2003, pp. 70-73.

Scher et al., Alternative Graft Materials for Hemodialysis Access, Seminars in Vascular Surgery, vol. 17, No. 1, Mar. 2004, pp. 19-24.

Wentling, Hemodialysis Catheters: Materials, Design and Manufacturing, Hemodialysis Vascular Access and Peritoneal Dialysis Access, vol. 142, 2004, pp. 112-127.

Olinger et al., Acute clinical hypocalcemic myocardial depression during rapid blood transfusion and postoperative hemodialysis: A preventable complication, The Journal of Thoracic and Cardiovascular Surgery, vol. 72, No. 4, Oct. 1976, pp. 503-511.

Flanigan et al., Regional Hemodialysis Anticoagulation: Hypertonic Tri-Sodium Citrate or Anticoagulant Citrate Dextrose-A, American Journal of Kidney Diseases, vol. 27, No. 4, Apr. 1996, pp. 519-524.

O'Farrell et al, Histologic Development of the Sheath that forms around long-term inplanted central venous catheters, Journal of Parenteral and Enteral Nutrition, vol. 20, No. 2, Mar. 1996, pp. 156-158.

Sheretz et al., Diagnosis of Triple-Lumen Catheter Infection: Comparison of Roll Plate, Sonication, and Flushing Methodologies, Journal of Clinical Microbiology, Mar. 1997, pp. 641-646.

Maki et al., Prevention of Central Venous Cathter-Related Bloodstream Infection by Use of an Antiseptic-Impregnated Catheter: A randomized, controlled trial, Annals of Internal Medicine, vol. 127, No. 4, Aug. 15, 1997, pp. 257-266.

Tang et al., "Use of surface-modifying macromolecules to enhance the biostability of segmented polyurethanes," J Biomed Mater Res. 35(3):371-81.

Baturovic et al., Filling Hemodialysis Catheters in the Interdialytic Period: Heparing Versus Citrate Versus Polygeline: A Prosepctive Randomized Study, Artificial Organs, 1998, pp. 945-947.

Ash et al., Concentrated Sodium Citrate (23%) for Catheter Lock, Hemodialysis International, 2000, pp. 22-31.

Sheretz et al., Education of Physicians-in-Training Can Decrease the Risk for Vascular Catheter Infection, Annals of Internal Medicine, Apr. 18, 2000, vol. 132 No. 8, pp. 641-648.

Shanks et al., Catheter lock solutions influence staphylococcal biofilm fomation on abiotic surfaces, Nephrology Dialysis Transplantation, Apr. 20, 2006, pp. 2247-2255.

Klement et al., Chronic performance of polyurethane catheters covalently coated with ATH complex: A rabbit jugular vein model, Biomaterials 27, Jun. 16, 2006, pp. 5107-5117.

Hanna et al., Comparative In Vitro Efficacies and Antimicrobial Dirabilities of Novel Antimicrobial Central Venous Catheters, Antimicrobial Agents and Chemotherapy, Oct. 2006, pp. 3283-3288.

Donelli et al., Vascular Catheter-Related Infection and Sepsis, Surgical Infections, vol. 7 Supplement 2, 2006, pp. S-25-S-27.

International Search Report PCT-US-99-03982_ISR dated Jul. 14, 1999.

* cited by examiner

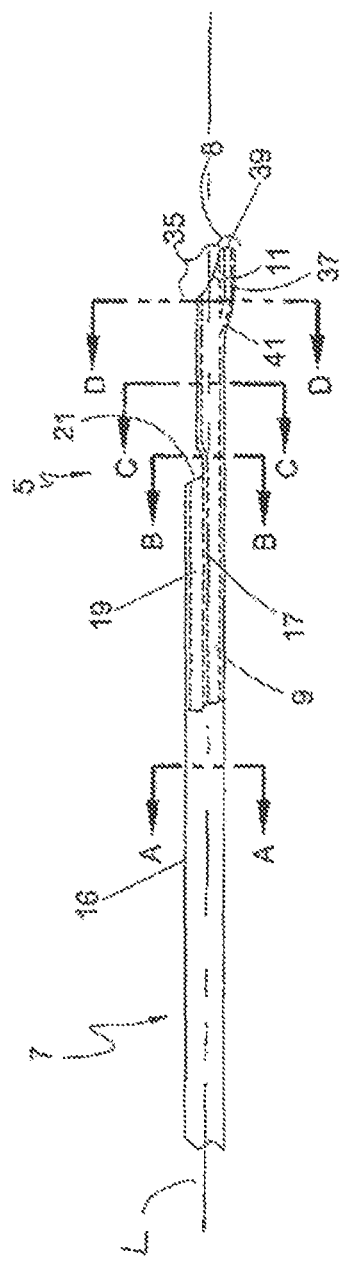
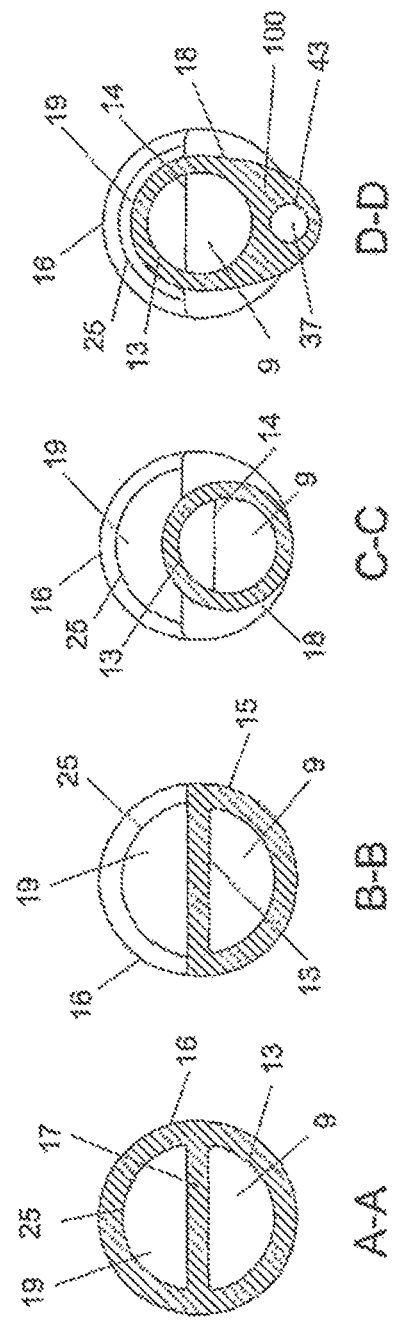
FIG. 2A
FIG. 2B

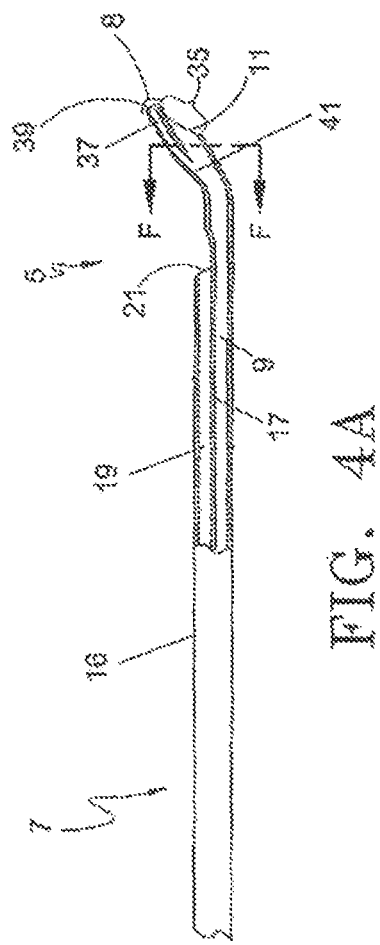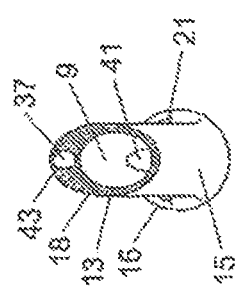

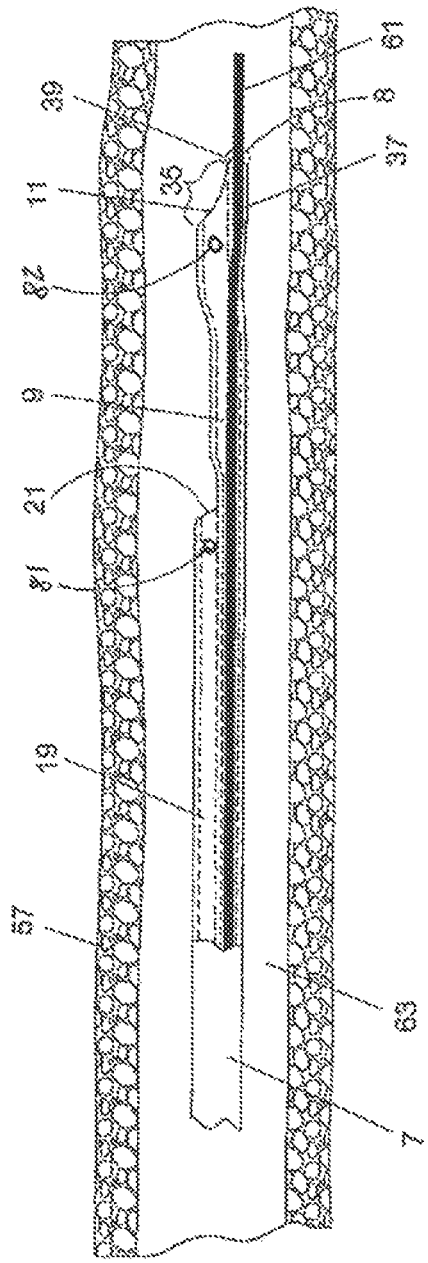

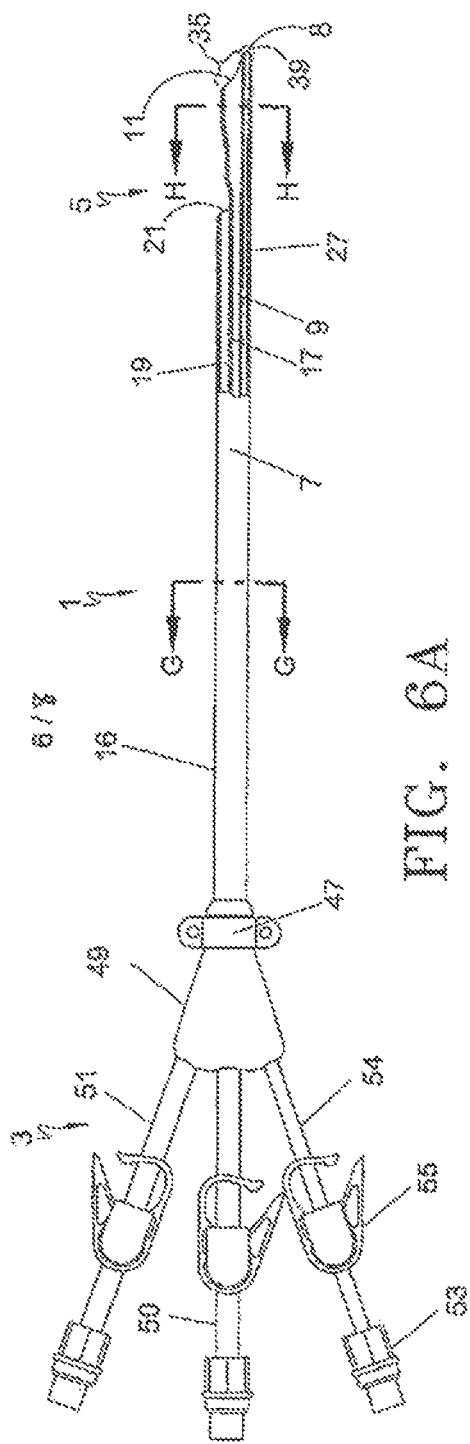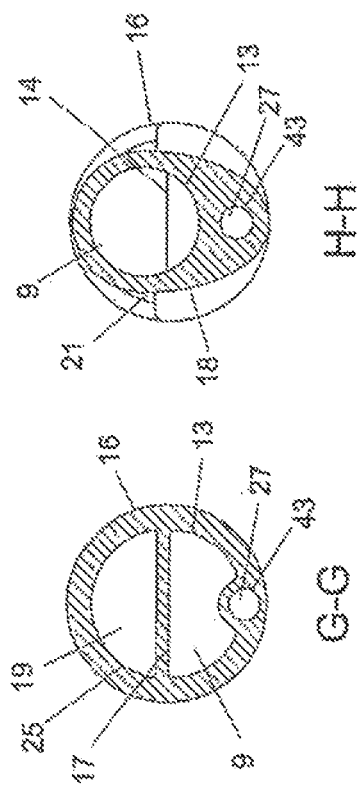
FIG. 6A
FIG. 6B

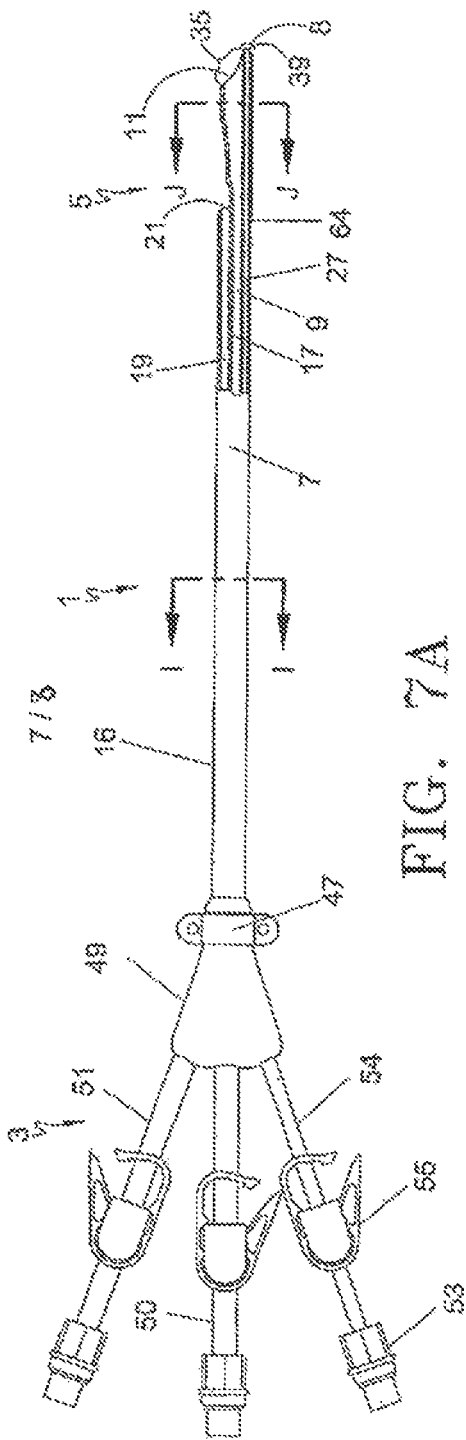
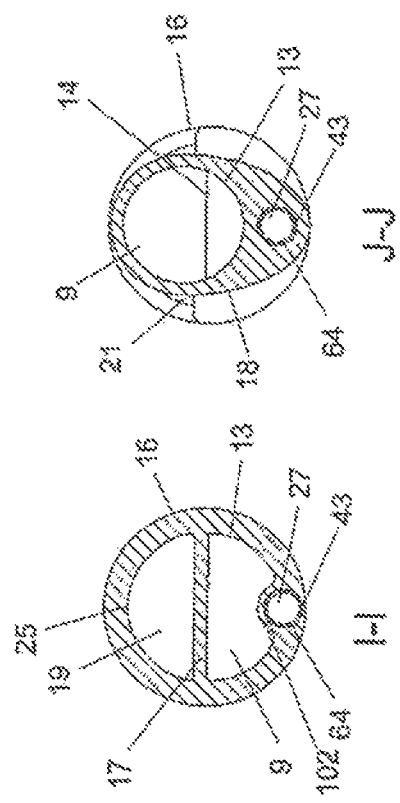
FIG. 7A
FIG. 7B

DIALYSIS CATHETERS WITH FLUOROPOLYMER ADDITIVES

RELATED APPLICATIONS

This application is a continuation of U.S. application Ser. No. 14/220,572 filed Mar. 20, 2014, which is a continuation-in-part of U.S. application Ser. No. 14/100,671, filed Dec. 9, 2013, which in turn claims priority to U.S. application Ser. No. 13/950,592, filed Jul. 25, 2013, now U.S. Pat. No. 8,603,070, which claims the benefit of U.S. Provisional Application Ser. No. 61/790,821 filed Mar. 15, 2013.

This application is also a continuation-in-part of U.S. application Ser. No. 14/151,267, filed Jan. 9, 2014, which in turn claims priority to U.S. application Ser. No. 12/392,220, filed Feb. 25, 2009, which is a division of U.S. application Ser. No. 11/557,369, filed Nov. 7, 2006 and now U.S. Pat. No. 8,317,773.

The entire disclosure of each of the foregoing applications is hereby incorporated by reference.

FIELD OF THE INVENTION

The present invention relates to catheters, and more specifically to dialysis catheters comprising fluoropolymer additives.

BACKGROUND

Hemodialysis (or more simply, "dialysis") is a method for removing waste products such as potassium and urea from the blood, such as in the case of renal failure. During hemodialysis, waste products that have accumulated in the blood because of kidney failure are transferred via mass transfer from the blood across a semi permeable dialysis membrane to a balanced salt solution. The efficiency of a hemodialysis procedure depends on the amount of blood brought into contact with the dialysis membrane. A flow of 250 milliliters of blood per minute under a pressure gradient of 100 millimeters of mercury is considered a minimum requirement for adequate dialysis. Over the past several years, flow rates between 350 milliliters per minute and 400 milliliters per minute have become common. These high flow rates and related pressures give rise to unique issues and challenges associated with dialysis catheters, as compared to other types of catheters.

The long hours and the frequency of the dialysis treatment in patients with renal failure require reliable, continued access to the venous system for blood exchange. Long-term venous access mechanisms commonly used for hemodialysis treatment include vascular access ports, dialysis grafts, and hemodialysis catheters. One type of blood treatment catheter that is well known in the art is a dual or triple-lumen hemodialysis catheter. These catheters are designed to provide long-term access to the venous system for dialysis. The dual-lumen catheter typically has an inflow lumen for withdrawing blood to be treated from a blood vessel and an outflow lumen for returning cleansed blood to the vessel. The distal segment of the catheter is typically positioned at the junction of the superior vena cava and right atrium to obtain a blood flow of sufficient volume to accommodate dialysis treatment requirements. This allows blood to be simultaneously withdrawn from one lumen, to flow into the dialysis circuit, and be returned via the other lumen. Triple lumen catheters function in a similar manner but have an additional smaller lumen which may be used for guidewire insertion, administration and withdrawal of fluids such as drugs or blood sampling, and for injection of contrast media required for imaging procedures.

To optimize blood flow rates during dialysis and reduce treatment times, catheters have been designed to maximize the cross-sectional lumen area of the inflow and outflow lumens. It is well known in the art that blood flow rates are negatively impacted if the cross-sectional area of the lumens does not remain essentially consistent and as large as possible throughout the entire length of the catheter from the proximal portion of the catheter to the distal portion of the catheter. Catheters with large, consistent luminal space typically have exit ports with blunt or flat-faced open tips, so as not to compromise the luminal area. Typically the exit port at the distal end of the catheter is cut at a 90-degree angle to the axis of the catheter.

One possible complication of dialysis catheters and other indwelling vascular medical devices is the aggregation of platelets on the surface of these devices, promoting thrombus formation, which may lead to catheter complications including catheter related blood stream infection and thrombosis. Particularly in the case of dialysis catheters, thrombus and sheath formation in and around the catheter may necessitate catheter removal because of its adverse impact upon flow rates and patient safety concerns. Generally, larger diameter catheters such as dialysis catheters are more likely than smaller diameter catheters to cause venous stasis and turbulent blood flow, which may be contributing factors to thrombus formation owing to characteristics such as increased catheter surface area and non-laminar blood flow. As a result, the catheter access site may become inaccessible, infected or otherwise damaged, thus leading to potentially life threatening complications if the ability to administer dialysis treatment is compromised. Moreover, any thrombus formed from catheter implantation could detach from the access site and migrate to other locations within the vascular, thus possibly causing other complications such as pulmonary embolisms. According to the Kidney Disease Outcomes Quality Initiative ("KDOQI") guidelines, more than half of patients having long-term catheters are removed within a year due to complications. Many of these patients have end-stage renal disease and rely upon the integrity of chronic dialysis catheters as the means through which they receive dialysis treatment. Because of the inherent risks associated with such long-term placement, dialysis catheters are associated with a relatively high rate of mortality.

Current treatments for chronic dialysis catheter complications include the use of thrombolytic fluids to disrupt thrombus formation, and the administration of intravenous antibiotics to combat infection. Both of these treatment modalities are designed to treat such complications rather than to prevent them. Moreover, a fluid lock, as known in the art, is used to prevent clot formation within the catheter between dialysis sessions. Typically, a heparin-saline fluid solution is infused into the full length of the catheter lumens. Recently, the use of coatings on the outer surfaces of dialysis catheters has been proposed for the prevention of thrombus formation. Although short term results of coated catheters have demonstrated a reduction in thrombus formation relative to uncoated catheters, longer term results are not as positive. It is believed that the decreased efficacy over time is at least partially attributable to the dissipation of the coating in situ.

As an alternative to catheter coatings, the permanent binding of biologically active moieties to catheter polymer chains or polymer surfaces has been studied. In U.S. Pat. No. 6,127,507, which is incorporated herein by reference for all purposes, it is proposed to use certain fluoroalkyl surface-modifying macromolecules in admixture with elastomers for the manufacture of blood-contacting medical devices. It is believed that the use of such macromolecules can result in a reduction in thrombosis formation on the medical device surfaces. While additives such as fluoropolymers and other materials may impart beneficial properties to implantable medical devices, their addition to polymeric materials used to manufacture the medical devices may also adversely impact mechanical properties. The purity of such additives may also adversely impact these properties.

There is a need to provide dialysis catheters that are capable of preventing thrombus formation during prolonged indwelling periods, thus avoiding the need for interventional treatments such as the administration of thrombolytic fluids and antibiotics. The prevention of thrombus would also result in a decrease in infections, an increase in dialysis efficacy, and a lower incidence of access loss due to premature catheter removal. Moreover, because complications relating to vascular access are the leading cause of hospitalization for hemodialysis patients, the prevention of thrombus formation on dialysis catheters would have a significant impact upon healthcare costs.

SUMMARY

The present invention addresses the needs discussed above by providing, in various embodiments, a dialysis catheter that comprises additives that comprise a fluoropolymer.

In certain aspects, the present invention comprises a dialysis catheter comprising multiple lumens. The catheter is made from a material that comprises additives that comprise a fluoropolymer comprising polyfluoro oligomeric groups.

DRAWINGS

In the drawings, like reference characters denote like elements across the different views. The drawings, which are not necessarily to scale, depict several exemplary embodiments and are not intended to limit the scope of the invention.

FIG. 2A is an enlarged partial cross-sectional view of the distal portion of the catheter of FIG. 1.

FIG. 2B illustrates three different cross-sectional views of the catheter shaft and one cross-sectional end view of the catheter of FIG. 2A along lines A-A, B-B, C-C, and D-D, respectively.

FIG. 4A is a partial cross-sectional view of an additional embodiment of the catheter with a curved distal portion.

FIG. 4B is a cross-sectional end view of the curved distal portion of the catheter of FIG. 4A.

FIG. 5A is a partial cross-sectional side view of the catheter of FIGS. 3A and 3B, while deployed inside a vessel with a guidewire inserted into the catheter.

FIG. 5B is a partial cross-sectional side view of the catheter of FIG. 5A after the guidewire has been removed from the catheter.

FIG. 6A is a plan view of a triple lumen catheter and a partial cross-sectional view of the distal portion.

FIG. 6B illustrates two different cross-sectional views of the catheter shaft of FIG. 6A, along lines G-G and H-H, respectively.

FIG. 7A is a plan view of an additional embodiment of a triple lumen catheter and a partial cross-sectional view of the distal portion.

FIG. 7B illustrates two different cross-sectional views of the catheter of FIG. 7A at the catheter shaft, along lines I-I and J-J, respectively.

DESCRIPTION OF THE PREFERRED EMBODIMENTS

Dialysis Catheters

In various embodiments, and referring to FIGS. 1-7B, presented herein is an exemplary vascular access catheter, such as a hemodialysis catheter.

Figure 1:
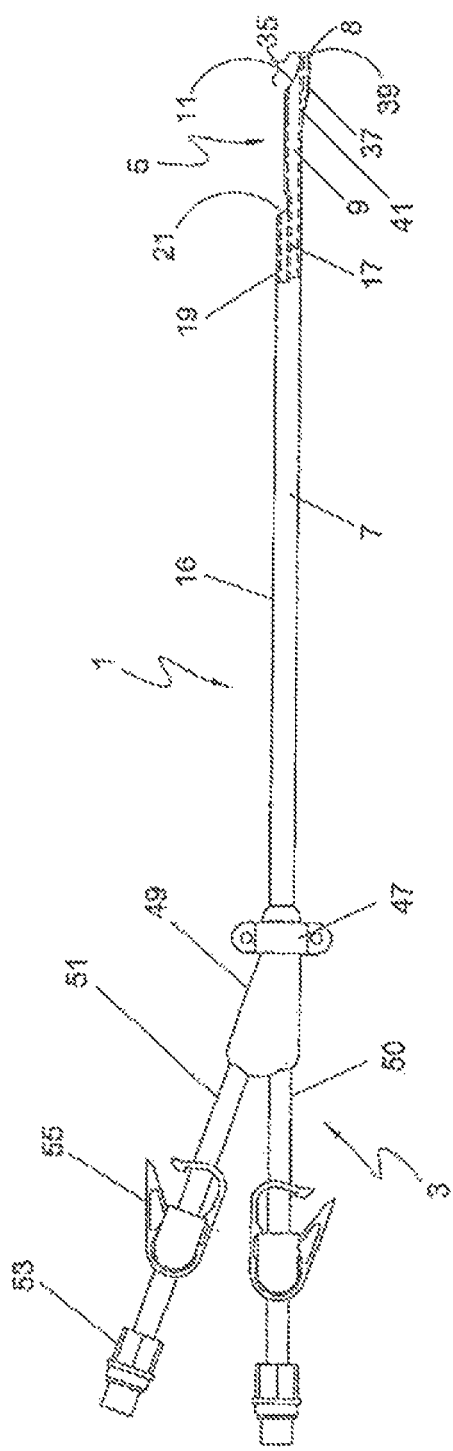
FIG. 1 is a plan view of the catheter and a partial cross-sectional view of the distal portion of the catheter.

FIG. 1 illustrates one embodiment of the hemodialysis catheter. In one aspect, the unitary catheter 1 has a proximal portion 3 and a distal portion 5. In this exemplary aspect, the distal portion 5 of the catheter 1 is substantially straight. In another aspect, the proximal portion 3 of the catheter 1 can be comprised of a bifurcate 49, a suture ring 47 coaxially arranged around the distal portion of the bifurcate 49, a pair of extension tubes 50, 51, extension tube clamps 55, and catheter hub connectors 53 for connection to a dialysis machine. In this aspect, the catheter shaft 7 extends from the bifurcate 49 to the distal tip 8 at the distal portion 5 of the catheter 1. In one aspect, as illustrated in FIG. 1, in the unstressed configuration, the shaft 1 is positioned in a single plane.

In one aspect, the catheter shaft 7 can be comprised of an outer wall 16 and at least a first lumen 9 and second lumen 19 extending longitudinally through substantially the entire length of the catheter shaft 7. Lumen 19 is fluidly connected with extension tube 51, and lumen 9 is fluidly connected with extension tube 50. Both extension tubes 50, 51 communicate through bifurcate 49. In one example, blood can be withdrawn from the vessel of the patient into lumen 19 where it is passed through the extension tube 51 into the dialysis machine. Blood can be returned to the patient through extension tube 50 into lumen 9, which exits through the distal aperture 11 into the vessel of the patient.

In one example, the outer diameter of the catheter 1 is approximately 0.203 inches, although, as one skilled in the art will appreciate, other diameter catheters are within the scope of this invention. In another example, and not meant to be limiting, the usable length of the catheter shaft 7, as measured from the distal end of bifurcate 49 to the distal tip 8, is between approximately 20 cm to 55 cm, depending on the patient's anatomy and physician preference. In one aspect the catheter shaft 7 usable length is between approximately 32 and 36 cm.

In one aspect, the catheter 1 is a unitary catheter composed of carbothane, but any suitable material may be used, such as, but not limited to, polyurethane or silicone. In another aspect, the catheter 1 may also contain a radiopaque material to enhance visibility under fluoroscopy. At least a portion of the catheter shaft 7 forms the distal portion 5 of the catheter 1. In a further aspect, the catheter shaft 7 can be configured such that the shaft 7 is more flexible at its distal portion 5 than its proximal portion 3. In one example, and not meant to be limiting, the distal portion 5 can have a reduced diameter and be formed with less material, compared to the proximal portion 3 of the catheter shaft 7, such that the distal portion 5 is relatively more flexible than the proximal portion 3. The increased relative flexibility of the distal portion 5 allows the distal portion 5 of the catheter to be more easily advanced through the vessel. The catheter shaft 7 may optionally be comprised of materials of different durometers to produce a shaft 7 with enhanced flexibility at the distal portion 5. In various other aspects, the catheter shaft 7 can be configured to be stiffer at the proximal portion 3 outside of the patient's body for durability and more flexible at the distal portion 5 to facilitate insertion of the catheter 1 and to provide a catheter 1 with an atraumatic tip, when placed within a vessel of the patient.

Figure 3A:
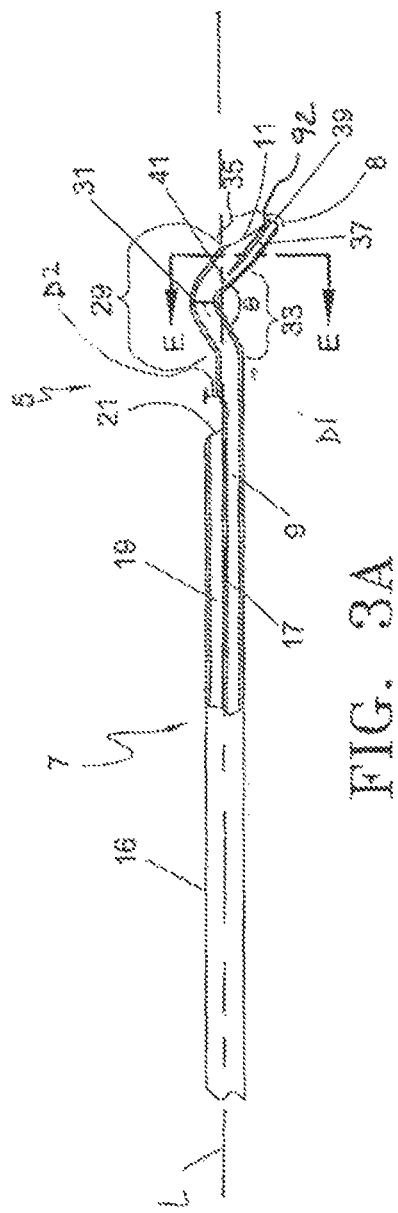
FIG. 3A is an enlarged partial cross-sectional view of an additional embodiment of the catheter with a curved distal portion.

In one additional aspect, the catheter 1 can have an inflow lumen 19 that is in fluid communication with an inflow aperture 21 that is defined in the exterior surface of the catheter 7 in the distal portion 5 of the catheter. The inflow lumen aperture 21 is in fluid communication with the second lumen 19 and is spaced proximally of the outflow lumen aperture 11. The inflow lumen 19 can be exemplarily used for withdrawal of blood from the patient. In one exemplary aspect, and as shown in FIG. 3A, the inflow aperture 21 can be sloped such that the cross-section of the inflow aperture 21 is forward-facing, and is positioned at an angle β greater than about 90 degrees relative to a longitudinal axis of the catheter shaft 7 (shown as line "L" in FIG. 3A). In another aspect, the catheter 1 has an outflow lumen 9 that can be exemplarily used for delivering cleansed blood back into the patient's circulatory system. In this example, blood exits the distal portion 5 of the catheter 1 through outflow aperture 11 that is defined in at least a portion of the distal end portion 35 that has a sloped face, distally of the inflow aperture 21, adjacent the distal tip 8 and in communication with the first lumen 9, as illustrated in FIGS. 1-7B. In yet another aspect, the two lumens 9 and 19 have inner walls 25 and 13, respectively, and are separated along their longitudinal length by, and share a common internal septum 17, illustrated along line A-A in FIG. 2B. One skilled in the art will appreciate that, although designated herein as inflow and outflow lumens, dialysis may be performed by reversing the blood flow through the lumens. Hence, the terms first lumen and second lumen may also be used herein to designate the interchangeability of the outflow and inflow lumens, respectively. In one aspect, the inflow lumen can have a D-shaped lumen configuration, and the outflow lumen 9 can have a partially D-shaped lumen configuration, as illustrated in FIGS. 2A-7B. Of course, it is contemplated that the lumens of the catheter 1 may have any suitable cross-sectional lumen shape as required for the particular use of the catheter 1.

In one aspect, the catheter 1 can have a third guidewire lumen 37 that is defined at least in the region of the distal portion 5 of the catheter 1 and has an inner wall 43. The guidewire lumen 37 extends proximally from aperture 39 defined therein the distal most portion of the sloped face of the distal end portion 35 of the catheter, distal of the first aperture 11, to aperture 41, defined therein the distal portion 5 of the catheter 1, where lumen 37 is joined to and terminates within outflow lumen 9. In one example, the third lumen 37 can have a generally smaller transverse cross-sectional area than lumens 19 and 9, as illustrated, for example, in FIGS. 4B, 6B, and 7B. In this aspect, the guidewire lumen 37 is configured for slidably receiving at least a portion of a guidewire (not shown). The guidewire lumen 37 provides a guidewire track for the guidewire to facilitate insertion of the catheter 1 through tissue into the target vessel and allows for improved guidewire insertion and tracking techniques, as described above. In one aspect, the guidewire lumen 37 extends a partial length d the catheter 1. In one exemplary aspect, and not meant to be limiting, the length of the guidewire lumen 37 may be between approximately 3 mm and 10 mm, preferably. In another aspect, the length of the guidewire lumen 37 may be between approximately 6 mm and 7 mm in length. In one exemplary aspect, the inner diameter of guidewire lumen 37 may be approximately 0.037 inches so as to accommodate a guidewire with an outer diameter of approximately 0.035 inches, such that it is positioned in close surrounding relationship to at least a portion of an inserted guidewire, as illustrated in FIG. 5A. It is contemplated that other dimensions may be used for the third lumen 37 and the guidewire. These dimensions allow the guidewire to be slidably received within the lumen 37, while minimizing space between the outer diameter of the guidewire and the inner diameter of the lumen 37. In one aspect, the third lumen 37 can be centered below the outflow lumen 9, as illustrated in FIGS. 2B, 4B, 6B, and 7B, such that the luminal cross sectional area of the outflow lumen 9 is not compromised. In this aspect, the distal aperture 39 of the third lumen 37 is defined in the distal portion 5 and is positioned distal to the outflow lumen aperture 11 at the distal most portion of the sloped face, such that the distal aperture faces distally away from the catheter shaft and is angled proximally away from the distal tip, as exemplarily illustrated in FIGS. 1 through 7B.

In one aspect, the distal tip 8, outflow aperture 11, and the guidewire exit aperture 39 define a sloped distal end portion 35 of the distal portion 5 of the catheter 1 in which at least a portion of the distal end portion 35 is sloped with a sloped open face, as illustrated in FIGS. 1 through 7B. "Sloped", as it pertains to the description herein, means that at least a portion of the distal end portion 35 has an angled edge that is not at a perpendicular angle relative to the longitudinal axis of the catheter 1, and could exemplarily include end portions 35 defined by flat, arcuate, or extended arcuate surfaces, in one aspect, the angled edge is angled proximally away from the distal tip 8 and is positioned at an acute angle γ relative to a longitudinal axis of the catheter shaft 7, illustrated in FIG. 5A. In one aspect, the sloped distal end portion 35 is positioned at approximately 30 degrees relative to the longitudinal axis of the catheter 1. In this aspect, the sloped distal end portion 35 that extends from the proximal most edge of the outflow lumen aperture 11 to the distal most edge of the third lumen 37 is approximately 5 mm, although the length will vary based on the angle of the slope. The acute angle γ of the sloped angled edge of at least a portion of the distal end portion 35 may between approximately 15 degrees and 75 degrees relative to the longitudinal axis of the catheter shaft 7. In another exemplary aspect, the sloped distal end portion 35 is approximately 30 degrees relative to the longitudinal axis of the catheter shaft 7.

In another exemplary aspect, the sloped distal end portion 35 can be configured to act as a dilator to provide enhanced insertion and tracking functionality without compromising flow rates, as will be explained in greater detail below.

The distal portion 5, defined herein as the length between the distal most edge of the inflow aperture 21 and the distal most edge of the guidewire exit aperture 39, can, in one non-limiting example, be approximately 2.5 cm, and in the depicted embodiment in FIG. 1, be substantially straight. In this example, the length between the distal most edge of the inflow aperture 21 and the proximal most edge of the outflow lumen aperture 11 is approximately 2 cm, which provides sufficient separation between the respective outflow and inflow two lumens 9, 19 to minimize re-circulation of blood during dialysis. As one skilled in the art will appreciate, recirculation is a complication of dialysis in which treated blood exiting from the outflow aperture 11 is pulled back into the catheter 1 through the inflow aperture 21 and re-processed by the dialysis machine. Recirculation reduces the efficiency of the cleansing process and results in inadequate dialysis if recirculation rates are too high. By spacing the inflow aperture 21 and outflow aperture 11 sufficiently apart, the recirculation rate during treatment is reduced to an acceptable level.

FIG. 2A illustrates an enlarged sectional view of the distal portion 5 of the catheter shaft 7 of FIG. 1. The outer wall 16 of the proximal portion 3 of the catheter shaft 7 surrounds an outflow lumen 9 and an inflow lumen 19, which are separated by a common internal septum 17. In one aspect, the outflow lumen 9 extends from the proximal most end of the catheter shaft 7 to aperture 11, defined therein sloped distal end portion 35. In one aspect, inflow lumen 19 extends distally from the proximal most end of catheter shaft 7 to inflow aperture 21.

In one aspect, the distal portion 5 of the catheter 1 includes a sloped distal end portion 35, which is comprised of distal tip 8, guidewire exit aperture 39, and outflow lumen aperture 11. The sloped profile of distal end portion 35 performs several functions. The forward-facing slope provides a tapered leading edge to facilitate insertion and advancement of the catheter 1. The forward-facing orientation of the slope is angled away from the vessel wall to minimize engagement with the vessel wall, once inserted. The distal-most leading edge of the sloped end portion 35 terminates in a guidewire exit aperture 39 for optimized guidewire tracking. Distal end portion 35 also includes a forward-facing, full size outflow lumen 11. Thus, in one aspect, the sloped distal end portion 35 combines the features of a distal end profile capable of tracking over a guidewire and dilating the insertion track as well as minimizing vessel wall contact with an aperture that is not reduced in cross-sectional area.

In one aspect, the partial transitional guidewire lumen 37 that is adapted for insertion of a guidewire (not shown), allows for ease of insertion of the guidewire into the catheter 1 and also allows ease of insertion of the catheter 1 into a vessel over the guidewire. The guidewire lumen 37 has an inner diameter of approximately 0.037 inches, which closely fits around an inserted guidewire of approximately 0.035 inches. These dimensions allow the guidewire to slide within the lumen 37, while eliminating space between the outer diameter of the guidewire and the inner diameter of the lumen 37. This enhanced guidewire tracking prevents tissue from being snagged during advancement of the catheter 1 into a target location, and the distal end portion 3 provides a dilating function, thereby reducing trauma and tissue disruption to the vessel. The guidewire and catheter 1 may therefore be easily inserted into a vessel without requiring the use of an introducer sheath. One skilled in the art will appreciate that the elimination of the introducer sheath reduces procedure time and costs, and minimizes the risk of air embolism due to absence of air gaps between the sheath and the catheter 1.

In another aspect, the transitional partial guidewire lumen 37 provides enhanced guidewire tracking, such that the outer diameter of the catheter 1 does not have to be increased to accommodate the partial lumen 37 adjacent to the outflow lumen aperture 11 at the distal most edge of the distal tip 8. This allows the effective cross-sectional area of the outflow lumen 9 to be maintained to be substantially uniform throughout the catheter 1 and provides for maximum blood flow.

In one aspect, FIG. 2B illustrates four different cross-sectional views of the catheter shaft 7 of one exemplary embodiment. The lumen configuration of the catheter 1 transitions from a double-D lumen, illustrated along line A-A, to a single-D lumen, illustrated along line B-B, to a single round outflow lumen 9 illustrated along line C-C, finally ending in a single round outflow lumen 9 at the distal most tip of the catheter 1, with a guidewire lumen 37 located adjacent the outflow lumen 9, which is illustrated along line D-D.

The first cross-sectional view, A-A, illustrates the double-D lumen configuration of the catheter shaft 7, which extends to just proximal of line B-B, where the inflow lumen 19 terminates at aperture 21. In one aspect, the lumens of the catheter 1 have a double-D configuration. In another aspect, the catheter 1 may have any suitable cross-sectional lumen shape as required for the particular use of the catheter 1. The advantage of a double-D lumen configuration is that it allows for maximal flow rates for a catheter 1 circular in cross-sectional profile, which fact is well known in the art. The outflow lumen 9 and the inflow lumen 19 are shown separated by a common internal septum 17. The outflow lumen 9 has an inner wall 13. The inflow lumen 19 has an inner wall 25. As illustrated in line A-A, the common internal septum 17 has a width of approximately 0.144 inches. In this exemplary embodiment, each double-D lumen may have a height of approximately 0.064 inches.

A cross-sectional view of line B-B in the distal portion 5 of the catheter 1 is also illustrated. Outer wall 16 and inner wall 25 define the inflow lumen 19, which is shown as an end view, terminating proximally of line B-B. The outflow lumen 9 extends distally of the inflow lumen 19, which terminates at inflow aperture 21, proximal to line B-B. At the termination point of inflow aperture 21, the double-D lumen also terminates and is continued as a single-D lumen 9.

At line C-C, the single-D shaped lumen has transitioned to a single round shaped outflow lumen 9. In this view, the transitional wall 14 represents the inner wall of the common internal septum 17 of the outflow lumen 9 at the double-D lumen section. At line C-C, the outflow lumen 9 has an inner diameter of approximately 0.095 inches and an outer diameter of approximately 0.140 inches. The rounded outer profile of the catheter shaft 7 at line C-C is of a smaller outer cross-sectional diameter than the cross-sectional diameter of the catheter shaft 7 at line B-B, which measures 0.203 inches. The reduced diameter facilitates insertion and advancement of the distal end of the catheter 1 through the tissue track and into the vessel.

A cross-sectional end view of the catheter 1, as taken along line D-D, is also illustrated. The cross-sectional end view, taken along lines D-D of FIG. 2B illustrates the guidewire lumen 37. Lumen 37 has a substantially circular shape defined by an inner wall 43. The inner diameter of the guidewire lumen 37 is approximately 0.037 inches. The guidewire lumen 37 is capable of receiving a guidewire that is approximately 0.035 inches.

In this aspect, lumen 37 is surrounded by an expanded guidewire wall segment 100 that separates lumen 37 from outflow lumen 9. Wall segment 100 may be formed using several techniques well known in the art including re-forming existing shaft material, or using a supplemental tip-forming or a molding process. In one aspect, lumen 37 can be positioned within guidewire wall segment 100 to ensure that the cross-sectional area of outflow lumen 9 at the sloped distal end portion 35 is substantially equivalent to the cross-sectional area of the proximal portion 3 of the lumen 9.

In one aspect, although the profiles of the lumens 19 and 9 of the catheter 1 change at different sections of the catheter 1, the transverse cross-sectional lumen areas are maintained throughout the length of the catheter 1. Specifically, the cross-sectional area of each of the double-D lumens, taken along line A-A, which is approximately 0.00702 square inches, is substantially equal to the cross-sectional area of the catheter 1 taken along line D-D, which is approximately 0.00708 square inches. This substantially equivalent cross-sectional area allows for optimal and consistent blood flow within the catheter 1 throughout treatment of the patient.

In addition, unlike current unitary catheter designs, the catheter 1 allows for insertion over a guidewire utilizing a leading distal end guidewire aperture without increasing the overall diameter of the catheter 1 and without compromising the cross-sectional luminal area of the outflow lumen 9. In one aspect, the cross-sectional diameter of the sloped distal portion 35 taken along the axis of the catheter shaft 7 is 0.160 inches, but may range from 0.150 to 0.180 inches. The reduced cross-sectional diameter of the outflow lumen 9 at line D-D, which is approximately 0.043 inches less than the proximal portion 3 of the catheter shaft 7, which has a cross-sectional diameter of approximately 0.203 inches, which thus facilitates insertion and advancement of the catheter 1 into a patient's body without compromising the cross-sectional luminal area of the outflow lumen 9.

Accordingly, in one aspect, a catheter 1 with a non-conical sloped dilating distal portion 35 is provided that maintains a consistent, uniform luminal area throughout the entire length of the catheter shaft 7. The substantially completely open sloped face geometry of the outflow lumen aperture 11 of the distal tip 8 allows for maximum blood flow because the cross-sectional area of the outflow lumen 9 is maintained from the proximal portion 3 to the distal portion 5 of the catheter 1, while the outer diameter of the catheter 1 is not increased. Because of its size and orientation, the outflow lumen aperture 11 is not likely to occlude, compared with typical conical-tapered or blunt tip catheters with smaller side wall lumen openings.

FIG. 3A illustrates another embodiment of the catheter 1. In this embodiment, the catheter shaft 7 has a double-D lumen configuration at its proximal portion 3, which transitions to a circular configuration with inflow and outflow apertures, similar to the embodiment illustrated in FIG. 1. The catheter shaft 7 of FIG. 3A is different from FIG. 1 in that it has a substantially curved distal portion 5 instead of a straight distal portion 5 in an unstressed state. The distal portion 5 of catheter shaft 7 may have any suitable curved shape configuration, including, but not limited to a curved, bent or semi-helical shape.

As further distinguished from the first embodiment of catheter 1 illustrated in FIGS. 1 and 2, at least a portion of the distal portion 5 of the catheter 1 that is substantially curved, as illustrated in FIGS. 1-7B, is defined by a guard portion 29. In this aspect, the guard portion 29 has an apex 31 that is located at the outermost point of the guard portion 29. As illustrated in FIG. 3A, in one aspect, the apex is positioned distally of the second lumen aperture 21. In yet another aspect, a portion of the guard portion 29 is spaced from the longitudinal axis of the catheter shaft 7 a distance D1 that is equal to or greater than the distance D2 that the outer wall 16 of the inflow aperture 21 is spaced from the longitudinal axis of the catheter shaft 7, as also illustrated in FIGS. 3A and 3B. The substantially curved distal portion 5 acts to guard lumen aperture 21 of the catheter 1 from being occluded, which in turn, maintains maximum blood flow, as described above. The guard portion 29 is also defined by an inner angle θ opposite the apex 31. In various aspects, it is contemplated that when the catheter shaft 7 is in the unstressed state, the inner angle θ of at least a portion of the distal portion 5 of the catheter may be between approximately 45 degrees and 135 degrees. In another aspect, the inner angle θ can be equal to or greater than about 90 degrees, depending on the curvature of the guard portion 29. In yet another aspect, the inner angle θ can be approximately 90 degrees. Optionally, the curved distal portion 5 may have substantially straight portions on either side of the inner angle θ, or the curved distal portion 5 may be a substantially continuous series of arcuate arcs.

Figure 3B:
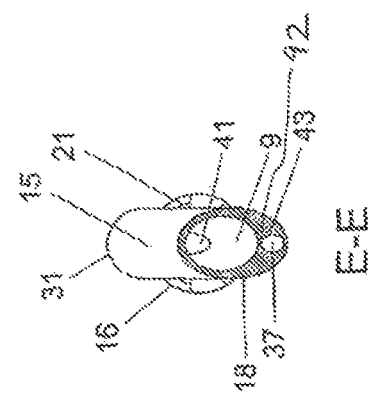
FIG. 3B is a cross-sectional end view of the curved distal portion of the catheter of FIG. 3A.

In one aspect, FIG. 3B illustrates the distal portion 5 of the catheter 1 of FIG. 3A along line E-E. As illustrated along line E-E of FIG. 3B, in one aspect, the apex 31 of the guard portion 29 can be configured so that, from a front elevation view, the distal end of the inflow aperture 21 is partially visible, being protected by portions of the apex 31 of the guard portion 29. The outer wall of the distal portion 5 of the catheter 1 transitions into a shared outer wall 18 of the outflow lumen 9 and the guidewire lumen 37, which has an inside wall 43. At least a portion of third lumen 37 and at least a portion of first lumen 41 are divided by and share a common wall 92. At least a portion of wall 92 is angled away from the longitudinal axis L of the catheter shaft along at least a portion of the length of the catheter shaft. In one aspect, at least a portion of the common internal wall 92 can be positioned on one side of the longitudinal axis L of the catheter shaft along at least a portion of the length of the catheter shaft.

In a further aspect, as shown in FIG. 3B, the space between the apex 31 and the outer wall 16 of the inflow aperture 21 can be configured to function as a guard to prevent aperture 21 from moving up against the vessel wall and at least partially or fully occluding the inflow aperture 21. In this aspect, as described above, the height D1 of apex 31 in relation to the longitudinal axis of catheter shaft 7 can be configured to be equal to or greater than the height D2 of the outer wall 16 of inflow aperture 21 in relation to the longitudinal axis of the catheter shaft 7, which should allow for the guard functionality. Thus, when the negative pressure of blood drawn into the inflow lumen 19 causes the catheter 1 to move toward the vessel wall, the apex 31 of the guard 29, rather than the inflow aperture 21, will abut up against the vessel wall.

In this aspect, the difference in height between the apex 31 of the guard portion 29 and the proximal most portion of the inflow aperture 21 helps the guard portion 29 to act as a guard to prevent inflow aperture 21 from contacting or resting against the vessel wall. The exemplified configuration of the guard portion 29 thus functions to ensure that aperture 21 remains positioned away from the vessel wall so as to avoid being partially or completely blocked and compromising outcome of the treatment session. As shown in the figures, apex 31, with its extended height, provides a separating barrier between the inflow aperture 21 and the outflow aperture 11, which acts to further minimize mixing cleansed and uncleansed blood during a dialysis session and decreases recirculation problems.

In another aspect, the guidewire lumen 37 shared outer wall 18, combined with the forward-facing orientation of the sloped distal end portion 35 also protects the outflow aperture 11 from being blocked if the catheter 1 comes into contact with the vessel wall. Referring to FIG. 3A, the catheter shaft 7 may be oriented such that it abuts the vessel wall at distal tip 8 rather than at apex 31. In this orientation, the distal tip 8 with guidewire exit aperture 39 contacts with the vessel wall and provides a spacing function similar to the guard 29 to protect the outflow aperture 11 from contacting and being blocked by the vessel wall. In this exemplified aspect, the forward-facing angle of the sloped distal end portion 35 is angled or oriented away from the vessel wall such that, as illustrated in FIG. 3A in the unstressed configuration, the shaft is positioned in a single plane, and the outflow aperture 11 will not become occluded by the vessel wall because it is protected by the distal tip 8.

In one aspect, as illustrated in FIG. 4A, catheter shaft 7 of can have a substantially bent distal portion 5 of the catheter 1 that defines an angle of greater than about 90 degrees relative to the longitudinal axis of the catheter shaft 7, such that the distal tip 8 is greater in height than the proximal most edge of the inflow lumen aperture 21. The clinical features described above in relation to the embodiment of the distal portion 5 of the catheter 1 illustrated in FIGS. 3A and 3B also apply to the embodiment illustrated in FIGS. 4A and 4B. In a further aspect, the embodiment illustrated in FIG. 4 provides a more direct blood flow path through lumen 9 which may enhance flow rates during dialysis.

A method of inserting the catheter 1 into a blood vessel is also disclosed herein and illustrated in FIGS. 5A and 5B. Although FIGS. 5A and 5B illustrate use of the catheter 1 embodied in FIGS. 3A and 3B, the method of inserting the catheter 1 may encompass the use of any of the embodiments of the catheter 1 described herein and illustrated in FIGS. 1 through 7. The method involves providing the catheter 1 described in any of FIGS. 1 through 7, inserting at least a portion of guidewire 61 into a vessel 57 in a patient body; inserting the proximal end of the guidewire 61 into the guidewire exit aperture 39 of the guidewire lumen 37; advancing the guidewire 61 through the guidewire lumen 37 and into the outflow lumen 9; inserting the catheter 1 into a vessel 57 in a patient body over the guidewire 61; positioning the distal portion of the catheter at a desired location within the target vessel 57; and removing the guidewire 61 from the catheter. If the catheter 1 of the embodiments illustrated in any of FIG. 3 or 4 is used, the method may further involve providing a catheter with a substantially curved or bent distal portion 5. The method may further involve straightening the distal portion of the catheter upon insertion of the guidewire 61 into the guidewire lumen 37. After the guidewire 61 is inserted into the guidewire lumen 37, the entire inserted guidewire 61 and the distal portion of the catheter become approximately parallel with the axis of the catheter shaft 7, as illustrated in FIG. 5A. Also shown in FIGS. 5A and 5B are optional side holes 81, 82 in second and first lumens 19, 9 of catheter 1.

FIG. 5A illustrates the tapered profile of sloped distal end portion 35 with its leading distal tip 8. This profile provides an atraumatic dilating function by gradually expanding the tissue track from the approximate size of a guidewire, typically 0.035 inches, to the slightly larger diameter of the distal tip 8, to the diameter of the catheter shaft 7 at the proximal most edge of outflow aperture 11, which is approximately 0.160 inches, to the maximum diameter of the catheter shaft 7 at inflow aperture 21, which is approximately 0.203 inches. Because of the dilating profile of the catheter 1, use of an introducer sheath is not necessary.

FIG. 5B illustrates a partial sectional side view of the catheter of FIG. 5A deployed within a vessel 57 inside of a patient body after the guidewire 61 has been removed from the catheter shaft 7. When the guidewire 61 is removed from the catheter shaft 7, the distal portion of the catheter 1 then recovers to its substantially curved configuration. In one aspect, the distal portion 5 of the catheter 1 has flexibility and a shaped memory, formed during the manufacturing process of the catheter, and is configured to allow the distal portion 5 of the catheter 1 to be substantially straightened when the guidewire 61 is inserted into and advanced through the third lumen 27/37, as illustrated FIG. 5A. This also allows the substantially curved distal portion 5 of the catheter 1 to recover toward its original curved unstressed state after the guidewire 61 is removed from the third lumen 27/37. Thus, the inner angle $\theta$ of the guard portion 29 recovers to an angle equal to or greater than about 90 degrees from the catheter shaft 7 axis.

In one aspect, when the catheter 1 is deployed in the vessel 57, the catheter 1 may migrate from the center of the vessel lumen 63 and abut up against the inner wall 59 of the vessel 57, as shown in FIG. 5B. The guard 29 contacts the inner vessel wall 59 at apex 31. The apex 31 of the guard portion 29 acts as a shield, preventing the aperture 21 from being occluded by vessel wall 59. It also provides a recirculation barrier between the inflow aperture 21 and the outflow aperture 11.

Also shown in FIG. 5B, the guard 29 also acts to orient outflow aperture 11 more centrally within the vessel 57 where blood volume is highest, thereby further minimizing recirculation rates, increasing the efficiency of the dialysis session, and reducing vessel wall 59 trauma caused by sustained contact with the catheter.

FIG. 6A illustrates yet another embodiment of the catheter 1 at line G-G. In this embodiment, the catheter 1 is identical to the embodiment illustrated in FIG. 1, except that the catheter 1 has a guidewire lumen 27 which extends substantially the entire length of the catheter 1 from the distal tip 8 to bifurcate 49, where the guidewire 27 lumen is fluidly connected with extension tube 54.

FIG. 6B illustrates the cross-sectional area of the catheter 1 of FIG. 6A taken along line G-G and H-H. The cross-sectional view along line G-G illustrates the outflow lumen 9 and the inflow lumen 19 separated by a common internal septum 17 and a guidewire lumen 27 defined by an outer wall 43. The outer diameter of the catheter 1 is approximately 0.203 inches, equivalent to previous embodiments. In a further aspect, to accommodate the guidewire lumen 27 within the partial double-D section of the catheter 1 without increasing the outer diameter of the catheter 1, the common internal septum 17 can be positioned slightly off-center. This allows the effective cross-sectional area of each lumen 19 and 9 to be substantially equalized, and aids in providing substantially equalized flow rates in both the inflow and outflow directions. In one non-limiting example, the resulting cross-sectional area of each lumen 19 and 9 is approximately 0.0065 square inches, which is approximately 0.0005 square inches less than the transitional guidewire lumen embodiments previously illustrated. This luminal area reduction of 0.0005 square inches is insignificant in terms of impact on flow rates. Thus, in this aspect, the cross-sectional luminal areas of the catheter 1 are maintained without having to increase the outer diameter of the catheter, as described above.

Along line H-H at the distal portion 5 of the catheter 1, the double-D lumen has transitioned to a single round outflow lumen 9. Also illustrated along line H-H, the cross-sectional lumen area of outflow lumen 9 is maintained at its largest diameter to distal aperture 11, as with the previous embodiments.

In one exemplary embodiment, illustrated in FIGS. 6A and 6B, it is contemplated that the guidewire lumen 27, which is fluidly connected with extension tube 54, may be used for the delivery of drugs, injections of fluids, such as contrast media, and for blood sampling, eliminating the need for the practitioner to place a secondary vascular access device. In addition, the cross-sectional luminal areas of previous embodiments are maintained without having to increase the outer diameter of the catheter 1. The substantially straight shape of the catheter 1 provides for direct blood flow paths and optimal flow rates in addition to minimal guidewire friction in comparison to curved embodiments. The continuous guidewire lumen 27 allows for the guidewire exchange or re-insertion, if necessary, after the catheter 1 has been placed in a vessel. The distal portion 5 of the catheter 1 is concentrically aligned within the outer circumference of the proximal portion 3 of the catheter shaft 7, as best illustrated in FIG. 6B, along line H-H. This alignment provides a structural barrier separating the inflow and outflow lumens 19 and 9, thereby minimizing recirculation rates during the dialysis session.

In one aspect as illustrated in FIGS. 7A and 7B, the guidewire lumen 27 may have a liner 64 placed along at least a portion of the inner wall 43 of the lumen 27. The liner 64 may reduce friction over the guidewire 61, thereby further enhancing guidewire 61 tracking capabilities of the lumen 27. The liner 64 may have a wall thickness of between approximately 0.002 and 0.005 inches, and is preferably constructed of a higher strength and/or a lower friction material than the catheter shaft 7, and may optionally include a fluoropolymer additive as described herein. The liner 64 disclosed herein may also be placed inside of the partial guidewire lumen 37 described herein in the previous embodiments and illustrated in FIGS. 1 through 5.

Figure 8:
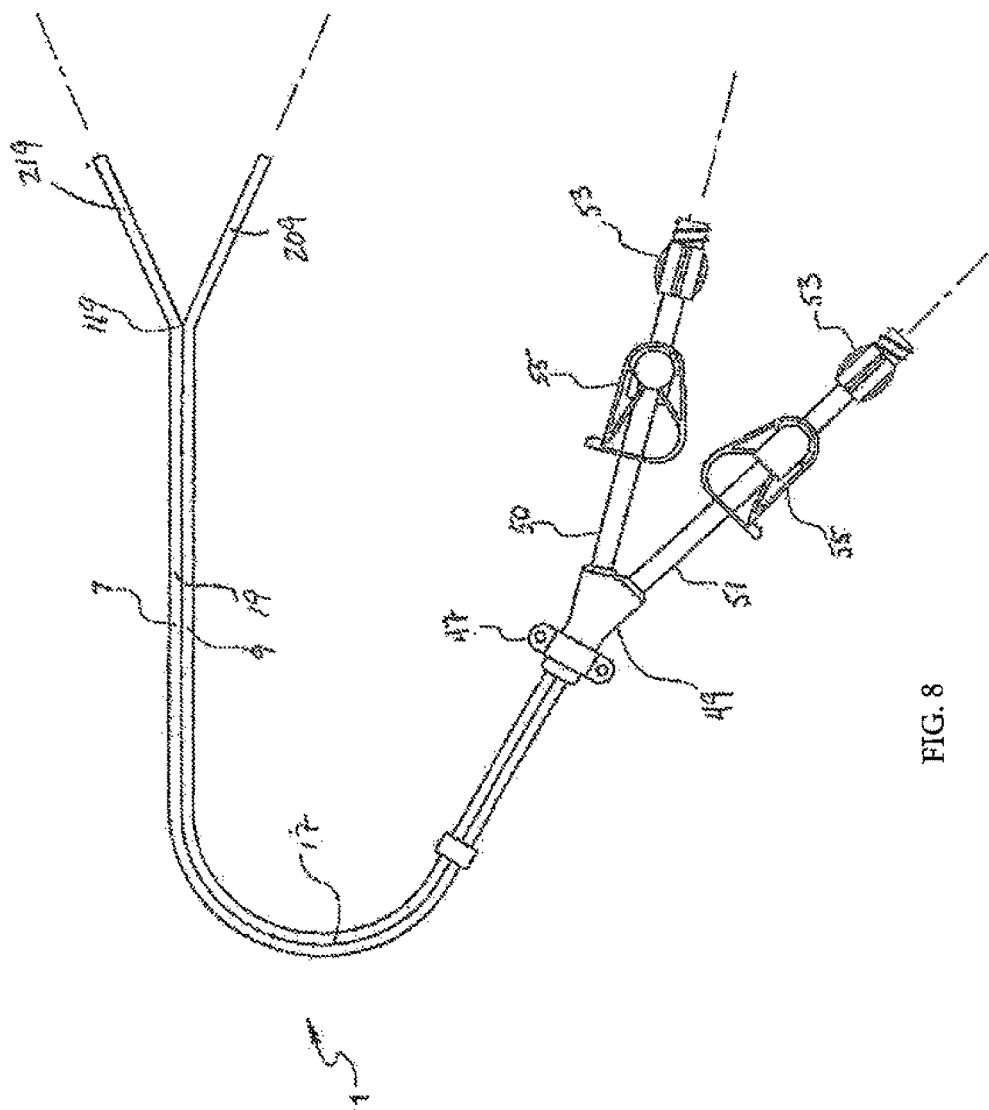
FIG. 8 illustrates alternate embodiments of the present invention that make use of specific dialysis catheter configurations.

While specific configurations of dialysis catheters are described herein, it should be appreciated that the present invention is applicable to any appropriate dialysis catheter configuration such as, for example, split tip configurations in which the distal portion 5 of the catheter 1 is split at point 119 into separate portions 209, 219 comprised of the outflow and inflow lumens 9, 19 as shown in FIG. 8; other dialysis catheter configurations such as those described in U.S. Pat. No. 5,718,692 to Schon et al., which is incorporated herein by reference in its entirety; and any other suitable dialysis catheter configuration.

Fluoropolymer Additives

Owing to their structures and compositions as set forth herein, the dialysis catheters of the present invention provide a unique and beneficial combination of anti-thrombogenic and mechanical properties. As used herein, the catheters of the present invention are said to be "anti-thrombogenic" or "thromboresistant" (which terms are used interchangeably in this specification) because they are more resistant to the accumulation of blood components than conventional catheter materials. While not wishing to be bound by theory, the inventors believe that the polymer compositions of the present invention provide a catheter surface and bulk that is unsuitable to the attachment or accumulation of blood components. As such, the catheters of the present invention achieve anti-thrombogenic properties not by drug delivery or by any therapeutically active means, but rather by providing a catheter surface and bulk to which blood components do not easily attach. Moreover, it should be understood that "anti-thrombogenic," as used herein, should not be limited to the complete elimination of thrombus buildup related to the catheter.

The catheters of the present invention preferably comprise polyurethane that include the additives, including fluoropolymers, as defined herein. One example of a suitable polyurethane material that is known in the art is CARBIOTHANE® (Lubrizol Advanced Materials, Inc., Cleveland, Ohio), which is a family of aliphatic, polycarbonate-based thermoplastic polyurethanes. Although polyurethanes are used as the preferred primary component in the materials used to make the catheters of the present invention, it is contemplated that other polymeric materials such as silicone may also be used.

The catheters of the present invention are manufactured from polymeric materials that comprise additives that are incorporated into the polymeric material. As used herein, "additives" refer to any materials that are added into the polymeric materials of the present invention to influence physical, mechanical, or other material properties, or to advantageously impact manufacturability or desired performance characteristics. Examples of known additives for polymeric materials include pigments (used synonymously herein with colorants), biostabilizers, plasticizers, nucleating agents fillers, radiopaque powders (or other forms), and materials in any form that enhance biocompatibility or other in vive performance characteristics.

An example of a fluoropolymer additive that is used in embodiments of the present invention is marketed under the trade name ENDEXO™ (Interface Biologies Inc., Toronto, Ontario Canada), which generally refers to a fluoropolymer additive material described in U.S. Pat. No. 6,127,507, which is incorporated herein for all purposes. As used herein, "fluoropolymer" means a fluorocarbon-based polymer, including oligomers, having carbon-fluorine bonds. In a preferred embodiment, the fluoropolymer used in the present invention is a fluoroalkyl fluoropolymer that is characterized by terminal polyfluoro oligomeric groups.

The additives used in the catheter compositions of the present invention may be distributed throughout the entirety of the catheter, or preferably in one or more sections of the catheter that come into contact with blood or other bodily fluids. For example, in the embodiment shown in FIG. 1, catheter shaft 7 contains the additives while extension tubes 50, 51 and bifurcate 49 optionally contain the additives. Moreover, the additives may be homogeneously distributed throughout the catheters of the present invention, or may be distributed such that the additive concentration varies along the catheter length or within the catheter wall thickness (i.e., stratified between the catheter outer wall and an inner lumen). It should be noted that the distal tip 8 of the catheters of the present invention may be formed at an angle with respect to the longitudinal axis of the catheter shaft 7 as shown in FIG. 3A, thus resulting in a significant increase in tip surface area (e.g., up to twofold) when compared with catheter tips that are cut orthogonally to the longitudinal axis. In some embodiments, the angle of the distal tip 8 is at a 45 degree angle relative to the longitudinal axis of the catheter shaft 7. The higher tip surface area inherently results in a higher potential for thrombus formation. Moreover, the non-linear catheter configurations of the present invention, as well as use of optional side holes 9, 19, such as those illustrated in FIGS. 3-5 may result in localized non-linear blood flow (e.g., eddies and/or relatively stagnant regions) in some areas immediately adjacent the catheter, thus possibly increasing the risk of thrombus formation. Moreover, the small size of lumens such as the guidewire lumen 37 and side holes 9, 19 may also be associated with an increased risk of thrombus formation. Side holes 9, 19 also present additional surface area for the possibility of thrombus formation. The additives of the present invention are useful to mitigate against these increased risk factors.

In addition to providing anti-thrombogenic properties, the additives of the present invention provide anti-adhesion properties to the catheter 1. Because, in certain embodiments, the additives are distributed substantially uniformly throughout one or more components of the catheter 1, the anti-thrombogenic and anti-adhesion properties exist throughout the catheter components that comprise the additives. As an example, owing to the additives, the inside surfaces of guidewire lumen 37 are characterized by anti-adhesion properties, thus easing the movement of a guidewire therethrough.

The preferred embodiment of a fluoropolymer additive is now described in detail. As described in U.S. Pat. No. 6,127,507, this additive may be referred to as a "surface modifying molecule" or "SMM." The surface modifying macromolecule has a central portion and terminal groups, the central portion being a member selected from the group consisting of a soft central portion and a hard central portion, the central portion having a molecular weight of less than 5,000 and including a segmented oligomeric copolymer unit including at least one polar segment and at least one hydrophobic segment, and the terminal groups including $\alpha$-$\omega$ terminal polyfluoro oligomeric groups. Preferably the oligomeric copolymer unit has a molecular weight of less than 5000, e.g. less than 2000 such as 200-1200. By the term "segmented" is meant a relatively short length of a repeating unit, generally less than about 10 monomeric units having, preferably, structural formulas such as ABAB, wherein A represents a polar hard segment chemically bonded to a soft block B. Preferably, the polyfluoro oligomeric group is a perfluoroalkyl group; and the polar hard segment is selected from the group consisting of a urethane, ester, amide, sulfonamide and carbonate. In a preferred aspect the invention provides a composition comprising in admixture a polyurethane elastomer and a compatible surface-modifying macromolecule in a surface-modifying enhancing amount, wherein said polyurethane elastomer has a molecular weight of at least twice the molecular weight of said SMM.

The SMM additives, when used in embodiments of the invention, are preferably synthesized in a manner that they contain a base polymer compatible segment and terminal hydrophobic fluorine components that are non-compatible with the base polymer. The compatible segment of the SMM is selected to provide an anchor for the SMM within the base polymer substrate upon admixture. While not being bound by theory, it is believed that the fluorine tails are responsible in part for carrying the SMM to the surface of the admixture, with the chemical resistant fluorine chains exposed out from the surface. The latter process is believed to be driven by the thermodynamic incompatibility of the fluorine tail with the polymer base substrate, as well as the tendency towards establishing a low surface energy at the mixture's surface. When the balance between anchoring and surface migration is achieved, the SMM remains stable at the surface of the polymer, while simultaneously altering surface properties. The utility of the additives of the invention versus other known macromolecular additives, lies in 1) the molecular arrangement of the amphipathic segments in the SMM chain, i.e. two—$\omega$ fluoro-tails, one at each end, with the polar segment sandwiched between them; 2) the molecular weight of the fluorine tails relative to that of the central segment and; 3) the ability of the materials to inhibit biodegradation of the base polymer when the fluoro-segments are stabilized at the interface, which provides improved blood compatibility and biostability of the base polymers. This latter improvement has not been previously achieved and/or demonstrated with any other family of amphipathic polymeric type surface modifying macromolecules.

The surface modifying macromolecules used in embodiments of the present invention significantly alter the surface chemistry of, for example, segmented polyurethanes, i.e. the SMMs migrate to the surface of the polymer mixture and exhibit a new hydrophobic domain. This new surface carries many of the attributes of the perfluoro-carbon chains and, therefore, can have improved hemocompatibility.

The SMM additives used in embodiments of the present invention are, for example, of use with linear or crosslinked polyurethane-based materials. By tailoring the central segment components of the SMM, the fluoropolymer additives can be applied inter alia to a wide range of polymer materials that include polymers synthesized with reagents that are of common knowledge in the field of polyurethanes.

There are no restrictions on the specific stoichiometry of the reagents used in the synthesis of the SMM fluoropolymers used in embodiments the present invention, the manner in which they are added to each other, the temperature, pressure or atmosphere under which they are synthesized or the use of catalysts in their reaction. However, the molecular weight of the soft segments (i.e., those parts of the central segment components that are not polar hard segments) are typically, between 200 and 5000. It is not desirable to simultaneously synthesize a SMM additive with the base polymer to which they are admixed, since the synthesis of the SMM additive is sensitive to reaction conditions. However, the SMM additives may be added to the synthesized base polymer, immediately following the latter's synthesis, in such a manner as to incorporate the SMM additives into the base polymer substrate prior to the final work-up of the polymer substrate.

Embodiments of SMM fluoropolymer additives used in the present invention may be synthesized using a multi-functional isocyanate, a multi-functional soft segment precursor reactive therewith, and a mono function polyfluoro-alcohol. The isocyanate is preferably, but not so limited to be di-functional in nature, in order to favor the formation of a linear SMM. Linear as opposed to branched or crosslinked SMM have better migration properties within the polyurethane substrate. A preferred diisocyanate for biomedical applications is 1,6-hexanediisocyanate. The soft segment precursor molecule is preferably di-functional in nature but not so limited to be di-functional, in order to favor the formation of a linear SMM. Again, linearity favors migration properties within the base polymer substrate. Examples of typical soft segment precursors include, polypropylene oxide polyols of molecular weight 1000, and polytetramethylene oxide diols of molecular weight 1000. SMM's are synthesized using a preliminary prepolymer method similar to the classical one used for polyurethanes. However, the subsequent step differs in that a chain extension is not carried out. A mono-functional oligomeric fluorinated alcohol is used to cap the prepolymer, rather than chain extend the prepolymer. The fluorinated alcohol preferably has a single fluoro-tail but is not limited to this feature. A general formula for the oligomeric fluoro-alcohol of use in the invention is $H-(OCH_2CH_2)_n-(CF_2)_m-CF_3$, wherein n can range from 1 to 10, but preferably ranges from 1 to 4, and m can range from 1 to 20 but preferably ranges from 2 to 12. A general guide for the selection of "n" relative to "m" is that "m" should be equal or greater to "2n" in order to minimize the likelihood of the $(OCH_2CH_2)_n$ segment displacing the $(CF_2)_m-CF_3$ from the surface following exposure to water, since the former is more hydrophilic than the fluorotail and will compete with the fluorotail for the surface. Without being bound by theory, the presence of the $(OCH_2CH_2)_n$ segment is believed to be important to the function of the SMM because it provides a highly mobile spacer segment between the fluorotail and the substrate. This is important in order to effectively expose the fluorosurface to, for example, an aqueous medium. Examples of typical oligomeric fluoroalcohols include various fractions BA-L, BA-N, FSO-100 and FSN-100 (DuPont de Nemours, Wilmington, Del.).

Examples of SMM fluoropolymer additives used in the present invention can be synthesized with different components and stoichiometry. Prior to synthesis, the isocyanate is, preferably, vacuum distilled to remove residual moisture. Soft segment precursors are degassed overnight to remove residual moisture and low molecular weight organics. In an example where BA-L is used as the fluoroalcohol, this reagent is fractionated into three fractions to reduce the distribution of molecules with different "m" values. This reduces the selective reaction of a fluoro-alcohol of a particular "m" value over another. The BA-L fractions were characterized as (i) a first fraction, herein called BA-L (Low), which is a clear liquid, distilled at 102.degree. C. and atmospheric pressure; (ii) a second fraction referred to as BA-L (Intermediate), which is a white semi-solid material, distilled between 70 and 80.degree. C. under a vacuum of 0.01 mm Hg pressure; and (iii) a last fraction referred to as BA-L (High) and is distilled between 80 and 100.degree. C. under a vacuum of 0.01 mm Hg as a very pale yellow solid. The selection of these fractions is somewhat arbitrary and it will be apparent to those skilled in the art that different fractions can be selected to alter the nature of the SMM in order to tailor the material for specific applications with base polymers. It is preferable to use organic solvents compatible with the chemical nature of the reagents in order to have good control over the characteristics of the final product. Typical organic solvents include dimethyl acetamide, acetone, tetrahydrofuran and dimethyl sulfoxide. A preferred reaction solvent is N,N-dimethylacetamide (DMAC, Aldrich Chemical Company, Milwaukee, Wis.). In view of the low reaction activity of some diisocyanates, e.g. HDI, with soft segment precursor diols, a catalyst is preferred for the synthesis. Typical catalysts are similar to those used in the synthesis of polyurethanes and, include, dibutyltin dilaurate, stannous octoate, N,N-diethylcyclohexylamine, N-methylmorpholine, tetramethylbutane-dianine and 1,4diazo (2,2,2) bicyclooctane.

In the first step of the preparation of an exemplary SMM fluoropolymer additive used in embodiments of the present invention, the isocyanate is added to the soft segment component and, optionally, catalyst to provide a prepolymer. Subsequently the fluoro-alcohol is added to the prepolymer and generally the mixture allowed to react overnight. The SMM polymer is precipitated in distilled water, washed to remove any residual fluoro-alcohol and dried. The SMM can be manipulated and handled for use with base polymers in the same manner as the polymers per se can be handled in the fabrication of article products. The SMM may be admixed with, for example, polyurethane base polymer 1) by compounding methods for subsequent extrusion or injection molding of articles; 2) by co-dissolving the polyurethane and SMM into a solvent of common compatibility for subsequent casting of an article in a mold or for spinning fibers to fabricate an article; or 3) by wetting the surface of a polyurethane with a solution of SMM in a solvent of common compatibility with the polyurethane to which the SMM solution is being applied.

The SMM fluoropolymer additives used in embodiments of the present invention provide, in one aspect, a series of fluorine-containing oligomeric surface modifying macromolecules. When used in admixture with, for example, a polyurethane, the SMM's inhibit polyurethane degradation by enzyme action. The SMMs are copolymers or terpolymers that have the ability to alter the surface chemistry and, hence, surface properties of a polymer and are synthesized in such a manner that (i) preferably, they have a lower molecular weight than the base material i.e. the polymer that requires protection from biodegradation and (ii) they contain a surface active segment containing (α-ω terminal polyfluoro groups.

SMM fluoropolymer additives used in embodiments of the present invention thus contain, preferably as α-ω terminal groups, fluoropolymeric segments comprising a sequential group of carbon atoms containing fluorine atoms and constituting an oligomeric chain. Preferred perfluorinated alcohols of use in the practice of the invention are those of the general formula $CF_3(CF_2)_nCH_2CH_2OH$, having a linear alkyl chain, wherein n is 5-9, most preferably $C_8F_{17}CH_2CH_2OH$. These monomers are commercially available under the trademark ZONYL (du Pont de Nemours, Wilmington, Del., USA) as homologous mixtures having varying degrees of fluoralkane chain lengths. One such preferred mixture available under the name BA-L has an average molecular weight of 443; fluorine content of 70%; S.G. 1.5@30.degree. C.; thickening point<25.degree. C. and a boiling range of 102-175.degree. C.@50 mm Hg.

The use of fluoropolymer additives, as described herein, is beneficial to achieving desired catheter anti-thrombogenic properties without the need for surface coatings. As such, the catheters of the present invention preferably do not contain heparin or surface coatings, thus minimizing the risk of complications associated with heparin use and the risk of decreasing thomboresistance properties over time due to coating wear. The additives, including the fluoropolymer are preferably present throughout the catheter material, including the outer surface, inner surface and even the cut catheter tip, thus preventing or minimizing thrombus formation on all catheter surfaces. The catheters of the present invention therefore avoid the need for interventional treatments such as the administration of thrombolytic fluids and antibiotics because the fluoropolymer additives prevent thrombus and sheath formation, thus decreasing infections, increasing dialysis efficacy, and decreasing the risk of access loss due to premature catheter removal. In addition, because the catheters of the present invention minimize clot adhesion to catheter wall surfaces, interluminal clots that may form from incomplete or faulty heparin-saline locks are removed with a lower pressure and force than required with conventional catheters. As such, use of the catheters of the present invention have a significant and positive impact on healthcare costs because of the decrease in hospitalizations due to the treatment of infections and other complications caused by thrombus formation on indwelling catheters.

In addition to fluoropolymer additives such as those described herein, other preferred additives used in the polyurethanes or other materials of the catheters of the present invention include radiopaque materials such as powders or other particulates. Suitable radiopaque additives include bismuth subcarbonate, bismuth oxychloride, bismuth trioxide, tungsten, and preferably barium sulfate. Other additives used in the present invention include colorants such as pigments, dyes, or other suitable materials.

The inventors have found that the amount and/or composition of additives used in the polymer compositions of the present invention are important for providing a unique and surprising combination of anti-thrombogenic properties and mechanical properties. For example, in some embodiments, the catheter comprises a polymeric material comprising a fluoropolymer comprising terminal polyfluoro-oligomeric groups, wherein the fluoropolymer is characterized by a polystyrene equivalent weight average molecular weight ($M_w$) greater than 13,000 Daltons (13 kDa). In particular embodiments, the fluoropolymer can contain less than 10% (w/w) (e.g., from 0% to 1.5%, 0% to 2%, 0.1% to 2.2%, 0.3% to 3%, 0% and 5%, or 0.5% to 5% (w/w)) trimer formed by reaction of one diisocyanate with two perfluorinated alcohols to form a low molecular weight fluoropolymer component containing no soft segment. In certain embodiments, the fluoropolymer can have a polystyrene equivalent weight average molar mass, $M_w$, of from 2,000 to 26,000 g/mole (e.g., 6.000±4,000, 8,000±4,000, 10,000±4,000, 12,000±4,000, 18,000±4,000, 20,000±4,000, 22,000±4,000, or 24,000±2,000 g/mole). In some embodiments, the fluoropolymer can have a polystyrene equivalent number average molar mass, $M_n$, of from 2,000 to 18,000 g/mole (e.g., 6,000±4,000, 8,000±4,000, 10,000±4,000, 13,000±2,000, 14,000±2,000, 15,000±2,000, or 16,000±2,000 g/mole). The fluoropolymer can have a polydispersity index of between 1.0 and 2.0 (e.g., a polydispersity of 1.1 to 1.4, 1.3 to 1.6, 1.35 to 1.55, 1.5 to 1.7, or 1.6 to 1.9). For example, the fluoropolymer can have a polystyrene equivalent weight average molar mass, $M_w$, of from 2,000 to 14,000 g/mole (e.g., 6,000±4,000, 8,000±4,000, or 12,000±2,000 g/mole), and/or a polystyrene equivalent number average molar mass, $M_n$, of from 2,000 to 12,000 g/mole (e.g., 6,000±4,000, 8,000±4,000, or 10,000±2.000 g/mole), and comprises between 0% and 3% (w/w) (e.g., from 0% to 1.5%, 0% to 2%, 0.1% to 2%, 0.1% to 2.2%, 0.3% to 2.2%, or 0.5% to 2.5% (w/w)) trimer. Alternatively, the fluoropolymer can have a polystyrene equivalent weight average molar mass, $M_w$, of from 14,000 to 26,000 g/mole (e.g., 18,000±4,000, 20,000±4,000, or 22,000±4,000 g/mole), and/or a polystyrene equivalent number average molar mass, $M_n$, of from 10,000 to 16,000 g/mole (e.g., 12,000±2,000 or 14,000±2,000 g/mole), and comprises between 0% and 3% (w/w) (e.g., from 0% to 1.5%, 0% to 2%, 0.1% to 2%, 0.1% to 2.2%, 0.3% to 2.2%, or 0.5% to 2.5% (w/w)) trimer. Fluoropolymer of desired size distribution and composition can be prepared, for example, by reducing the amount of diisocyanate used to make the fluoropolymer and/or by fractionating (i.e., by column chromatograph, dialysis, or extraction) the fluoropolymer.

In certain embodiments, the present invention comprises catheter materials comprising polyurethane and additives comprising a radiopaque material and a fluoropolymer comprising terminal polyfluoro-oligomeric groups. The amount of additives within the catheter material is up to about 44 weight percent (wt %), preferably up to about 40 wt %, more preferably up to about 35 wt %, more preferably up to about 33 wt %, more preferably up to about 25 wt %, and most preferably up to about 22 wt % of the catheter material. The amount of the fluoropolymer within the additives is preferably 1.5 wt %-2.5 wt % of the catheter material, preferably up to 2.0 wt %. The amount of radiopaque material within the additives, if used, is preferably 15 wt %-25 wt %, and more preferably up to 20 wt % of the catheter material, though amounts may vary depending on the material used. For instance, barium-based fillers can be used at concentrations of up to 40 wt %, while bismuth-based fillers are used at concentrations up to 30 wt % and metallic fillers such as tungsten can be used at up to 80 wt % concentrations. The amount of colorant within the additives, if used, is preferably 2 wt % of the catheter material, and more preferably up to about 0.2 wt % of the catheter material.

The inventors have found that the 14.5-15.5 Fr catheters described herein, when manufactured within these compositional limitations, possess outstanding anti-thrombogenic properties and mechanical properties. For example, such catheters having wall thicknesses within the range of 0.015 to 0.050 inches effectively minimized thrombus formation in in vivo, blood-containing environments while remaining intact and structurally sound when used for dialysis procedures. With flow rates up to 400 mL/min, catheters of the present invention are able to withstand pressures of up to about 240 mmHg (arterial negative pressure) and 220 mmHg (positive venous pressure), depending upon catheter length and diameter. As such, the catheters of the present invention offer exceptional long-term thrombus prevention while having sufficient wall strength to withstand (without collapsing, bursting or otherwise being compromised) the high positive and negative pressures associated with dialysis procedures.

In certain embodiments, the present invention comprises catheter materials comprising polyurethane and a fluoropolymer additive comprising polyfluoro-oligomeric groups, wherein the fluoropolymer is preferably characterized by a polystyrene equivalent weight average molecular weight ($M_w$) greater than 13,000 Daltons (13 kDa), more preferably 14-26 kDa. Moreover, the fluoropolymer additive is preferably characterized by a polydispersity index that is between 1.0 and 2.0, more preferably between 1.0 and 1.5. As used herein, "polydispersity index" is used synonymously with heterogeneity index and is calculated by the polystyrene equivalent weight average molecular weight ($M_w$) divided by the polystyrene equivalent number average molecular weight ($M_a$).

An exemplary catheter according to one embodiment of the invention includes a multi-lumen catheter shaft 7, a bifurcate 49, and a plurality of extension tubes, 50, 51, for instance as shown in FIG. 1 and as discussed above. The composition and relevant dimensions of the various components of this exemplary catheter are listed in Table 1, below:

TABLE 1

Exemplary compositions of catheter shaft, extension tubes, and bifurcate.

| | Catheter Shaft 7 | Extension Tubes 50, 51 | Bifurcate 49 |
|---|---|---|---|
| Polyurethane | Carbothane 95A | Carbothane 95A | Carbothane 95A |
| Fluoropolymer molecular weight | 14,000-26,000 g/mol | 14,000-26,000 g/mol | 14,000-26,000 g/mol |
| Fluoropolymer polydispersity index | 1.0-2.0 | 1.0-2.0 | 1.0-2.0 |
| Fluoropolymer weight percentage | 2% +/−0.6 | 2% +/−0.8 | 2% +/−0.10 |
| radiopaque material | barium sulfate | none | barium sulfate |
| radiopaque material wt % | 20% (+/−3) | none | 20% (+/−3) |
| weight percentage of colorant | 0.20% | 0.00% | 0.20% |

Because the fluoropolymer additive is incorporated into the catheter material itself, rather than being used as a coating on the catheter, it does not wear or vary in efficacy over time and it is present on all catheter surfaces (i.e., all exterior, interior luminal, and end surfaces). The effect is a reduction in thrombus formation in all catheter lumen sizes, including smaller lumens such as guidewire lumens that are particularly susceptible to clotting because of their size.

The catheters of the present invention have other additional benefits and advantages not mentioned above. Catheter size, material and implant duration have an impact on the occurrence and extent of vessel trauma. Generally, larger and stiffer catheters may result in a higher risk of vessel trauma and thrombus buildup. The use of the additives of in the present invention result in a decrease in catheter stiffness, thus reducing vessel trauma and possible resultant localized stenosis and thrombus buildup. Additionally, a softer catheter is generally easier to advance through curved or complex vessels without resulting in kinking or pinch-off syndrome. As is known in the art, however, the use of softer catheter materials may result in manufacturing difficulties because such materials may not be sufficiently flowable to be molded or otherwise worked without void creation. The inventors have found it possible to mold and form the catheters of the present invention by heating to 30° C.-60° C.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein, which equivalent are also intended to be encompassed by the claims.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

What is claimed is:

1. A catheter comprising:
a catheter shaft (a) defining first and second shaft lumens and (b) forming a distal portion of the catheter, wherein the distal portion of the catheter includes a distal end portion having a distal tip and at least a portion of the distal end portion is substantially sloped with a sloped face that is angled proximally away from the distal tip and is positioned at an acute angle relative to a longitudinal axis of the catheter shaft; and
wherein the catheter comprises a fluoropolymer comprising polyfluoro oligomeric groups; wherein the fluoropolymer is characterized by a weight average molecular weight (Mw) greater than 13 kDa; and wherein the fluoropolymer comprises a trimer in an amount greater than 0 and less than 5.0 percent by weight of the fluoropolymer, wherein the trimer is formed by a reaction of one equivalent of diisocyanate with two equivalents of a perfluorinated alcohol to form a low molecular weight fluoropolymer component containing no soft segment.

2. The catheter of claim 1, wherein the polydispersity index of said fluoropolymer is less than or equal to 2.0.

3. The catheter of claim 1, wherein said fluoropolymer is characterized by a weight average molecular weight (Mw) within the range of 14 kDa to 26 kDa.

4. The catheter of claim 1, wherein said catheter comprises a polycarbonate-based polyurethane.

5. The catheter of claim 1, wherein said catheter shaft further comprises about 17 weight percent to about 30 weight percent of a radiopaque material.

6. The catheter of claim 1, wherein said catheter comprises about 1.4 weight percent to about 2.6 weight percent of said fluoropolymer.

7. The catheter of claim 5, wherein said radiopaque material comprises barium sulfate.

8. The catheter of claim 1, wherein said catheter shaft comprises a third shaft lumen configured to selectively receive at least a portion of a guidewire, and wherein at least a portion of the third shaft lumen shares a common wall with at least a portion of the first shaft lumen.

9. The catheter of claim 1, wherein said catheter shaft has an outer wall thickness within the range of 0.015-0.050 inches.

10. The catheter of claim 1, further comprising a plurality of extension tubes fluidly connected to the shaft, and wherein said extension tubes comprise a fluoropolymer comprising polyfluoro oligomeric groups characterized by a weight average molecular weight (Mw) greater than 13 kDa.

11. A catheter comprising:
a shaft comprising a first lumen, a second lumen, and a distal tip, each of said first and second lumens separated by a common internal septum and terminating at respective first and second apertures; and
an apex in the shaft defining a portion of the first lumen distal to the second aperture;
wherein the catheter comprises a fluoropolymer comprising polyfluoro oligomeric groups, said fluoropolymer characterized by a weight average molecular weight (Mw) greater than 13 kDa; wherein the fluoropolymer comprises a trimer in an amount greater than 0 and less than 5.0 percent by weight of the fluoropolymer, wherein the trimer is formed by a reaction of one equivalent of diisocyanate with two equivalents of a perfluorinated alcohol to form a low molecular weight fluoropolymer component containing no soft segment; and wherein a distance between said apex and a longitudinal axis of said shaft is equal to or greater than a distance between an outer wall defining said second lumen and said longitudinal axis of said shaft.

12. The catheter of claim 11, wherein an outer wall of said first lumen is characterized by an inner angle opposite said apex, said inner angle being between approximately 45 degrees and 135 degrees.

13. The catheter of claim 12, wherein said inner angle is equal to or greater than about 90 degrees.

14. The catheter of claim 11, further comprising a guidewire lumen.

15. The catheter of claim 11, wherein at least one of said apex and said distal tip is configured to abut a wall of a blood vessel wall when said shaft is inserted into said blood vessel.

16. The catheter of claim 11, wherein the polydispersity index of said fluoropolymer is less than or equal to 2.0.

17. The catheter of claim 11, wherein said fluoropolymer is characterized by a weight average molecular weight (Mw) within the range of 14 kDa to 26 kDa.

18. The catheter of claim 11, wherein said catheter comprises a polycarbonate-based polyurethane.

19. The catheter of claim 11, wherein said catheter further comprises about 20 weight percent to about 30 weight percent of a radiopaque material.

20. The catheter of claim 11, wherein said catheter comprises about 1.5 weight percent to about 2.5 weight percent of said fluoropolymer.

21. The catheter of claim 11, further comprising a plurality of extension tubes fluidly connected to the shaft, and wherein said extension tubes comprise a fluoropolymer comprising polyfluoro oligomeric groups characterized by a weight average molecule weight (Mw) greater than 13 kDa.

* * * * *